United States Patent [19]

Schneerson et al.

[11] Patent Number: 5,445,817
[45] Date of Patent: Aug. 29, 1995

[54] PERTUSSIS TOXIN USED AS A CARRIER PROTEIN WITH NON-CHARGED SACCHARIDES IN CONJUGATE VACCINES

[75] Inventors: Rachel Schneerson, Bethesda, Md.; Lily Levi, Haifa, Israel; John B. Robbins, Chevy Chase, Md.

[73] Assignee: The United States of America as represented by the Department of Health and Human Services, Washington, D.C.

[21] Appl. No.: 932,960

[22] Filed: Aug. 21, 1992

[51] Int. Cl.⁶ .................. A61K 39/385; A61K 39/09; A61K 39/10

[52] U.S. Cl. ............................ 424/194.1; 424/197.11; 424/244.1; 424/240.1; 424/831; 530/402; 530/403

[58] Field of Search ............. 424/88, 92, 244.1, 240.1, 424/194.1, 197.11, 831; 530/395, 402, 403, 411

[56] References Cited

U.S. PATENT DOCUMENTS

| | | | |
|---|---|---|---|
| 4,693,891 | 9/1987 | Collins et al. | 424/170.1 |
| 4,774,086 | 9/1988 | Quentin-Miller et al. | 424/240.1 |
| 4,784,589 | 11/1988 | Robinson et al. | 424/254.1 |

(List continued on next page.)

FOREIGN PATENT DOCUMENTS

| | | |
|---|---|---|
| 0186576 | 7/1986 | European Pat. Off. |
| 0208375 | 1/1987 | European Pat. Off. |
| 0245045 | 11/1987 | European Pat. Off. |

(List continued on next page.)

OTHER PUBLICATIONS

Kallings et al, Lancet I: 955–960, 1988.
Schneerson, R., et al, Infection and Immunbity 52(2):519–528, 1986.
Sekura, R D, et al, Pertussis Toxin: Affinity Purification of a New ADP–Ribosyltransferase J. Biol Chem 23(2):14647–14651, 1983.
Robbins, J B, et al, Journal of Infectious Diseases 148(6):1136–1159, 1983.
Bauminger S, et al, Methods in Enzymology 70:151–159, 1980.
R. Schneerson, et al., 1984. "Serum Antibody Responses of Juvenile and Infant Rhesus Monkeys Injected with *Haemophilus influenzae* Type b and Pneumococcus Type 6A Capsular Polysaccharide-Protein Conjugates". *Infect. and Immun.*, 45(3):582–591.
Schreurs, A. J. M. et al., 1983, "Bacterial cell wall components decrease the number of guinea pig lung beta-adrenoceptors." *Chem. Abstrs.*, 98(15), Abstract No. 123740x, 11 Apr. 1983.
P. Anderson et al., 1989, "Human adult immunogeniciety of protein-coupled pneumococcal capsular anti- (List continued on next page.)

*Primary Examiner*—Christine M. Nucker
*Assistant Examiner*—Julie Krsek-Staples
*Attorney, Agent, or Firm*—Morgan & Finnegan

[57] ABSTRACT

A medically important and useful conjugate comprising pertussis toxin (PT), or another antigen having similar physico-chemical properties, as the carrier protein component, coupled to a neutral or non-charged saccharide, particularly, the capsular polysaccharide of *Streptococcus pneumoniae* type 14 (Pn14), for use as an effective, non-toxic, and highly immunogenic vaccine is described. The invention is directed to a novel synthetic scheme wherein PT and like proteins, and a derivative of Pn14, and the like, were coupled at acidic pH via carbodiimide-mediated condensation to produce an immunogenic conjugate. The coupling procedure yielded a Pn14-PT conjugate in which the PT component was rendered non-toxic and both the PT and Pn14 components were immunogenic, as determined by the production of protective levels of both type-specific and neutralizing antibodies in mammals. The Pn14-PT conjugate was used as an immunogen at levels estimated to be protective in humans and stands to provide an effective, safe, and potent human vaccine.

11 Claims, No Drawings

U.S. PATENT DOCUMENTS

| | | | |
|---|---|---|---|
| 4,788,058 | 11/1988 | Parton et al. | 424/240.1 |
| 5,045,203 | 9/1991 | Quentin-Miller et al. | 210/635 |
| 5,153,312 | 10/1992 | Porro | 530/405 |

FOREIGN PATENT DOCUMENTS

| | | |
|---|---|---|
| 0471177 | 2/1992 | European Pat. Off. . |
| 0497525 | 8/1992 | European Pat. Off. . |
| 2144128 | 2/1985 | United Kingdom . |

OTHER PUBLICATIONS gens of serotypes prevalent in otitis media," *Pediatr. Infect. Dis.*, 8:S50–S53.

A. F. M. Verheul et al., 1989, "Modulation of the immune response to pneumococcal type 14 capsular polysaccharide–protein conjugates by the adjuvant Quil A depends on the properties of the conjugates," *Infect. Immun.*, 57:1078–1083.

J. H. M. Wigert et al., 1991, "Immunogenicity of *Streptococcus pneumoniae* type 14 capsular polysaccharide: Influence of carriers and adjuvants on isotype distribution," *Infect. Immun.*, 59:2750–2757.

M. Porro et al., 1985, "A semisynthetic glycoconjugate antigen prepared by chemical glycosylation of pertussis toxin by a meningococcal group C polysaccharide oligosaccharide hapten". Proceedings of the Fourth International Symposium on Pertussis. Joint IABS/WHO.

J. B. Robbins et al., 1990, "Polysaccharide–protein conjugates: A new generation of vaccines," *J. Infect. Dis.*, 161:821–832.

E. C. Beuvery et al., 1982, "Comparison of the induction of immunoglobulin M and G antibodies in mice with purified pneumococcal type 3 and meningococcal Group C polysaccharides and their protein conjugates," *Infect. Immun.*, 37:15–22.

C. Y. Chu et al., 1983, "Further studies on the immunogenicity of *Haemophilus influenzae* type b and pneumococcal type 6A polysaccharide–protein conjugates," *Infect. Immun.*, 40:245–256.

A. Fattom et al., 1990, "Serum antibody response in adult volunteers elicited by injection of *Streptococcus pneumoniae* Type 12F polysaccharide alone or conjugated to diphtheria toxoid," *Infect. Immun.*, 58:2309–2312.

C. C. A. M. Peeters et al., 1991, "A comparative study of the immunogenicity of pneumococcal Type 4 polysaccharide and oligosaccharide tetanus toxoid conjugates in adult mice," *J. Immunol.*, 146:4308–4314.

J. C. Paton et al., 1991, "Purification and immunogenicity of genetically obtained pneumolysin toxoids and their conjugation to *Streptococcus pneumoniae* type 19F polysaccharide," *Infect. Immun.*, 59:2297–2304.

M. Pittman, 1979, Pertussis toxin: "The cause of the harmful effects and prolonged immunity of whopping cough. A hypothesis," *Rev. Infect. Dis.*, 1:401–412.

M. Pittman, 1975, "Determination of the histamine sensitizing unitage of pertussis vaccine," *J. Biol. Stand.*, 3:185–191.

M. Oda et al., 1984, "Protective activities of the filamentous–hemagglutinin and the lymphocytosis–promoting factor of *Bordetella pertussis* in mice," *J. Infect. Dis.*, 150:823–833.

H. Sato et al., 1984, "*Bordetella pertussis* infection in mice: Correlation of specific antibodies against two antigens, pertussis toxin and filamentous hemagglutinin with mouse protectivity in intracerebral or aerosol challaenge system," *Infect. Immun.*, 46:415–421.

P. Olin et al., 1989, "The efficacy of acellular pertussis vaccine," *JAMA*, 261:560.

R. D. Sekura et al., 1988, "Clinical, metabolic, and antibody responses of adult volunteers to an investigational vaccine composed of pertussis toxin inactivated by hydrogen peroxide,"*J. Pediatr.*, 113:806–813.

G. Zackrisson et al., "History of whooping cough in nonvaccinated Swedish children, related to serum antibodies to pertussis toxin and filamentous hemagglutinin," *J. Pediatr.*, 116:190–194.

M. Granstrom et al., 1985, "Neutralizing antibodies to pertussis toxin in whooping cough," *J. Infect. Dis.*, 151:646–649.

M. Granstrom et al., 1991, "Specific immunoglobulin for treatment of whopping cough," *Lancet*, 338:1230–1233.

R. Austrian et al., 1977, "The bacteriology of pneumococcal otitis media." *John s Hopkins Medical J.*, 141:104–111.

J. M. Borgono et al., 1978, "Vaccination and revaccination with polyvalent pneumococcal polysaccharide vaccines in adults and infants," *Proc. Soc. Exp. Biol. Med.*, 157:148–154.

E. Morch, 1943, "Serological studies on the Pneumococci," *Eds. E. Munksgaard & H. Milford, Oxford University Press*, p. 160.

P. H. Makela, 1980, "Pneumococcal vaccine and otitis media," *Lancet*, II:547–551.

J. B. Robbins et al., 1983, "Considerations for formulating the second-generation pneumococcal capsular polysaccharide vaccine with emphasis on the cross-relative types within groups," *J. Infect. Dis.*, 148:1136–1159.

G. Bolan et al., 1986, "Pneumococcal vaccine efficacy in selected populations in the United States," *Ann. Int. Med.*, 104:1–6.

PERTUSSIS TOXIN USED AS A CARRIER PROTEIN WITH NON-CHARGED SACCHARIDES IN CONJUGATE VACCINES

FIELD OF THE INVENTION

The present invention relates to the production of clinically acceptable carrier protein-saccharide (e.g. polysaccharide and oligosaccharide) conjugates which are useful as effective vaccines, especially in infants and young children, for the induction of protective levels of antibodies against medically important pathogens, particularly, for example, the capsular polysaccharide of *Streptococcus pneumoniae* type 14 (hereinafter also referred to as pneumococcus type 14 or Pn14), and pertussis toxin (hereinafter also referred to as PT) produced by the *Bordetella pertussis* bacterium.

BACKGROUND OF THE INVENTION

The development of safe and effective vaccines is essential to prevent systemic infections, which continue to cause high rates of morbidity and mortality throughout the world. To prevent and ultimately eradicate a wide variety of systemic infections caused by bacterial pathogens or microorganisms with neutral polysaccharides, universal immunization of infants and adults with suitable vaccines, which are capable of eliciting safe, effective, and long-lasting immunity, is needed. Because the incidence of diseases caused by invasive bacterial pathogens is highest in children under two years of age, effective immunization must begin early and optimally be completed within the first half year of life. Subsequent booster immunizations at about fifteen months and five years may also be advocated.

Surface polysaccharides serve as essential virulence factors and protective antigens for invasive bacteria which infect the bloodstream as their primary pathogenic event (39, 41). These surface antigens include capsular polysaccharides of both Gram-negative and Gram-positive bacteria and the lipopolysaccharides of Gram-negative bacteria. Although most of these purified polysaccharides elicit protective levels of antibodies in healthy adults, both capsular polysaccharides and lipopolysaccharides have immunologic properties or pharmacologic activities that limit their use as vaccines. Capsular polysaccharides are known in the medical literature and are polymers of sugars, sugar acids, amino sugars, polyhydric alcohols, and sugar phosphates. The capsular polymers may contain linkages other than glycosidic linkages and constituents other than the abovementioned sugars.

The immunologic properties of capsular polysaccharides which limit their use in infants and children, the age group with the highest attack rate of systemic infections caused by capsular pathogens, is their age-related immunogenicity (i.e. the ability to elicit the production of antibodies) and their T cell independence (i.e. lack of a statistically significant rise in antibody levels following re-injection or booster response). Pn14 has the abovementioned properties which exclude its usefulness as a vaccine for infants and children. That is, by itself, Pn14 does not elicit protective levels of antibodies in children up to four years of age (age-related immunogenicity) and does not elicit a booster response following m-injection (T cell independence) (40, 56, 57). In healthy adults, injection of Pn14 elicits protective levels of antibodies; however, re-injection of Pn14 does not elicit a booster response (40, 57).

To provide protection against some capsulated bacterial pathogens of infants and children, established vaccines have been used which comprise proteins such as diphtheria or tetanus toxoids or other potentially protective antigens such as the toxoid of *Pseudomonas aeruginosa* exotoxin A or pneumococcus hemolysin attached to polysaccharides (1, 6, 10, 12, 15, 22, 33, 41, 49). It has been estimated that induction of protective levels of antibodies to approximately ten bacterial polysaccharides would potentially result in a substantial decrease in serious infections of infants (2–4). However, complex formulation of conjugates containing the approximately six to ten polysaccharides of medical interest would require more carder proteins than are currently available as vaccines, for example, diphtheria toxoid or tetanus toxoid. There is a limit to the number of saccharides that can be bound to a single protein because of the possibility of immune suppression due to carrier protein overload of the immune system. Others have worked with conjugates for prevention of systemic infections caused by medically important organisms such as *Haemophilus infiuenzae* type b or various serotypes of *Streptococcus pneumoniae* (6, 10, 15, 33, 34, 41, 49, 50) in an effort to afford immune protection in mammals.

*Streptococcus pneumoniae* (pneumococci) are a major cause of otitis media, pneumonia, meningitis, and other invasive diseases which cause mortality and morbidity throughout the world (2–4, 7, 40, 47). Otitis media is the most common disease caused by this pathogen in infants and children (2–4, 26, 40). Several large surveys have reported that of the 87 known capsular polysaccharide types (i.e. serotypes) of *Streptococcus pneumoniae*, Pn14 is the one type which is isolated most frequently from patients of all ages (2–4, 40). The capsular polysaccharide of *Streptococcus pneumoniae* type 14 is also called pneumococcus type 14 and is composed of a neutral (i.e. a non-charged or non-negatively charged), repeating tetrasaccharide (24):

$$\rightarrow 6)\text{-}\beta\text{-D-GlcpNAc-}(1 \rightarrow 3)\text{-}\beta\text{-D-Galp-}(1 \rightarrow 4)\text{-}\beta\text{-D-Glcp-}(1 \rightarrow$$

$$\begin{array}{c} 4 \\ \uparrow \\ 1 \\ | \\ \beta\text{-D-Galp} \end{array}$$

Pneumococcus type 14 is a comparatively poor immunogen among the pneumococcus capsular polysaccharides. Pn14 is a less-than-optimal immunogen in the 23-valent vaccine for adults (2, 7, 40, 54, 55). Also, Pn14 does not elicit protective levels of antibodies in human infants and young children—the age groups with the highest attack rate of diseases caused by *Streptococcus pneumoniae* (1, 2, 15, 40, 56, 57). In addition, except for humans, *Streptococcus pneumoniae* type 14 is of limited virulence and is not pathogenic for animals, including mice. Pn14 elicits serum antibodies in humans only (25, 27).

*Bordetella pertussis*, the microorganism that causes whooping cough or pertussis, is a highly contagious upper respiratory pathogen (36). *Bordetella pertussis* produces a protein toxin called pertussis toxin (PT) which elicits a variety of severe physiological and cellular responses including induction of lymphocytosis, sensitization to the lethal effects of histamine, and stimulation of insulin secretion, to name a few (28-31, 36, 42, 43, 45). The physiologic and cellular actions of PT appear to be mediated by interference with cyclic nucleotides (45). Laboratory and clinical data have shown that pertussis toxin is both a virulence factor (36) and a protective antigen (10, 31, 33, 43, 47). An inactivated toxin (i.e. a toxoid) is an essential component of acellular vaccines for pertussis (17, 18, 31, 32, 36, 46). Both laboratory and clinical data have shown that serum antibodies confer protective immunity to pertussis (29, 30, 32, 42) and have provided evidence that pertussis toxin is essential for vaccine-induced protective immunity to pertussis.

Although PT can elicit the production of protective antibodies, PT has several properties which make it difficult to use as a carder protein. For example, PT is mostly insoluble at pH values between about 4 and 8, which are optimal for carrying out many conventional coupling reaction procedures. In addition, PT is composed of six polypeptides that are not covalently bound.

The synthesis of saccharide-protein conjugate vaccines has been reported since 1929 (5, 23). The experimental data from these reports established the principle that the immunogenicity (i.e. the ability to elicit serum antibodies) of a saccharide may be increased following its covalent attachment to a protein. However, these initial synthetic schemes used chemicals and routes of immunization in animals that are neither appropriate for use nor suitable for clinical investigation in humans. The synthesis of a clinically-acceptable saccharide-protein conjugate vaccine was first reported in 1980 (53). The 1980 report described the covalent binding of saccharide to protein by first reacting the linking molecule, adipic acid dihydrazide (ADH), with the protein. Next, this derivatized protein was bound to the polysaccharide. In a later scheme using *Haemophilus infiuenzae* type b and pneumococcal 6A polysaccharide, the polysaccharide was first derivatized with ADH and then was covalently bound to the protein (10).

Since 1980, several other synthetic schemes for preparing saccharide-protein conjugates have been reported (reviewed in 41). ADH has been used as a linking molecule for a number of saccharides other than Pn14, which have properties different from those of Pn14 (11, 12, 13, 22, 34, 52).

Conjugates of Pn14 have been reported using reductive amination to couple Pn14 to diptheria toxoid (1) or using carbodiimide-mediated coupling at pH greater than 4, followed by overnight dialysis at neutral pH (49, 50).

The production of a saccharide conjugate with pertussis toxin was reported as a presentation at a conference (38). The saccharide group, group C capsular polysaccharide of *Neisseria meningitidis* (meningococcus), was an oligosaccharide prepared by acid pyrolysis. The resultant saccharide was derivatized with the N-hydroxysuccinimide ester of adipic acid. The derivative was dissolved in dimethyl sulfoxide and was added to pertussis toxin which was also dissolved in dimethyl sulfoxide. The reaction mixture (i.e. the derivatized oligosaccharide and pertussis toxin) was then passed through a Sephadex G-100 column. Polyacrylamide gel electrophoresis (PAGE) of the reaction mixture showed two major components which differed from the profiles of the group C meningococcal oligsaccharide and from that of PT. A critical reading of this conference report shows that the sections purporting to show data and results provided no experimental proof that the saccharide was covalently bound (i.e. chemically bonded) to the PT. Thus, there is a lack of experimental evidence that chemical bonding of the saccharide to the PT occurred. Further, although it is well known that dimethyl sulfoxide is an organic solvent which has the property of denaturing proteins, the effect of dimethyl sulfoxide on the migration of PT in PAGE was neither mentioned nor identified. Gel chromatography was used to compare the alleged conjugate with PT alone. Using this technique, there was no difference in the chromatographic profiles of the alleged conjugate and the PT. Moreover, an unconventional technique described in the report as "affinity" electrophoresis was used to show that PT was chemically combined with the group C meningococcal oligosaccharide. However, the results of the "affinity" electrophoresis were neither shown by illustration nor described in the text. Further, the report provided no mention of the use of controls, such as other structurally similar polysaccharides or linear homopolymers that are negatively-charged. Lastly, the report did not consider or mention injecting the "conjugate" into animals or humans to verify that 1) a serum antibody response was elicited by the "conjugate"; 2) serum antibodies were generated against both the group C meningococcal oligsaccharide and the PT; or 3) that serum antibody response to the saccharide had improved or changed. Both unsupported and uncontrolled data, and conclusions drawn without proper experimental findings, lead to the determination that no valid scientific evidence was presented to show that the group C meningococcal saccharide was bound to PT, or that the reported preparation had enhanced the immunogenicity of the saccharide.

U.S. Pat. No. 5,085,862, issued Feb. 4, 1992, discloses the production of defined mutant holotoxins of pertussis toxin using site directed mutagenesis. The toxin analogues as described are immunoprotective in mice. U.S. Pat. No. 4,788,058, issued Nov. 29, 1988, describes a method of preparing an immunogenic preparation of pertussis toxin treated in the form of an intimate admixture with filamentous hemagglutinins. U.S. Pat. No. 4,673,574, issued Jun. 16, 1987, describes an immunogenic conjugate which is the reductive amination product of a capsular polymer fragment having a reducing end and derived from a bacterial capsular polymer of a bacterial pathogen. The problems associated with the use of PT, such as its insolubility under conditions of neutral pH, are neither addressed nor surmounted.

LIST OF REFERENCES

1. Anderson, P., and R. Betts. 1989. Human adult immunogenicity of protein-coupled pneumococcal capsular antigens of serotypes prevalent in otitis media. Pediatr. Infect. Dis. 8:S50–S53.
2. Austrian, R. 1981. Some observations on the pneumococcal vaccine and on the current status of pneumococcal disease and its prevention. Rev. Infect. Dis. 3:51–57.

3. Austrian, R. 1984. Pneumococcal Infection. In: *Bacterial Vaccines*. Ed. Rene Germanier, Academic Press, New York. pp 287.
4. Austrian, R., V. M. Howie and J. H. Ploussard. 1977. The bacteriology of pneumococcal otitis media. Johns Hopkins Medical J., 141:104–111.
5. Avery, O. T. and W. Goebel. 1929. Chemo-immunological studies on conjugated carbohydrate-proteins. II. Immunological specificity of synthetic sugar-proteins. J. Exp. Med. 50:521–533.
6. Beuvery, E. C., F. V. Rossum and J. Nagel. 1982. Comparison of the induction of immunoglobulin M and G antibodies in mice with purified pneumococcal type 3 and meningococcal group C polysaccharides and their protein conjugates. Infect. and Immun. 37:15–22.
7. Bolan, G., C. V. Broome, R. R. Facklam, B. D. Flikaytis, D. W. Fraser and W. F. Schlech. 1985. Pneumococcal vaccine efficacy in selected populations in the United States. Ann. Int. Med. 104:1–6.
8. Broome, C. V., and D. W. Fraser. 1981. Pertussis in the United States. A look at vaccine efficacy. J. Infect. Dis. 144:187–190.
9. Bums, D. L., J. G. Kenimer and C. R. Manelark. 1987. Role of the A subunit of pertussis toxin in alteration of Chinese hamster ovary cell morphology. Infect. and Immun. 55:24–28.
10. Chu, C. Y., R. Schneerson, J. B. Robbins and S. C. Rastogi. 1983. Further studies on the immunogenicity of Haemophilus infiuenzae type b and pneumococcal type 6A polysaccharide-protein conjugates. Infect. and Immun. 40:245–256.
11. Chu, C.-Y., B. Liu, D. Watson, S. C. Szu, D. Bryla, J. Shiloach, R. Schneerson, and J. B. Robbins. 1992. Preparation, characterization, and immunogenicity of conjugates composed of the O-specific polysaccharide of *Shigella dysenteriae* type 1 (Shiga's Bacillus) bound to tetanus toxoid. Infect. and Immun. 59 4450–4458.
12. Devi, S. J. N., J. B. Robbins, and R. Schneerson. 1991. Antibodies to poly [2→8] αN-acetylneuraminic acid are elicited by immunization of mice with *Escherichia coli* K92 conjugates: Potential vaccines for groups B and C menigococci and *E. coli* K1. Proc. Natl. Acad. Sci. USA. 88:7175–7179.
13. Devi, S. J. N., R. Schneerson, W. Egan, T. J. Ulrich, D. Bryla, J. B. Robbins, J. E. Bennett. 1991. *Cryptococcus neoforrnans* serotype A glucoronoxylomannan-protein conjugate vaccines: Synthesis, characterization, and immunogenicity. Infect. and Immun. 59:3700–3707.
14. Egan, W., R. Schneerson, K. E. Werner, and G. Zon. 1982. Structural studies and chemistry of bacterial capsular polysaccharides. Investigation of phosphodiester-linked capsular polysaccharides isolated from *Haemophilus influenzae* types a, b, c, and f: NMR spectroscopic identification and chemical modification of end groups and the nature of base-catalyzed hydrolytic depolymerization. J. Am. Chem. Soc. 104:2898–291010.
15. Fattom, A., C. Lue, S. C. Szu, J. Mestecky, G. Schiffman, D. Bryla, W. F. Vann, D. Watson, J. B. Robbins and R. Schneerson. 1990. Immune response adult volunteers elicited by injection of the *Streptococcus pneumoniae* type 12F polysaccharide alone or conjugated to diphtheria toxoid. Infect. and Immun. 58:2309–2312.
16. Gillenius, P., E. Jaatmaa, P. Askelof, M. Granstrom and M. Tiru. 1982. The standardization of an asssay for pertussis toxin in microplate culture of Chinese hamster ovary cells. J. Biol. Stand. 10:1–9.
17. Granstrom, M., M. Blenow, P. Askelof, P. L. Gillenius and P. Olin. 1984. Antibody response to pertussis toxin in whooping cough and pertussis vaccination. J. Infect. Dis. 151:646–650.
18. Granstrom, M., A. M. Olinder-Nielsen, P. Holmblad, A. Mark and K. Hanngren. 1991. Specific immunoglobulin for treatment of whooping cough. Lancet, 338:1230–1234.
19. Inman, J. K. and H. M. Dintzis. 1969. The derivatization of cross-linked polysaccharide beands. Controlled induction of functional groups for the purpose of special purpose biochemical absorbents. Biochemistry. 8:4074–4080
20. Kolb, J-P., E. Genot, E. Petit-Koskas, N. Paul-Eugene and B. Dugas. 1990. Effect of bacterial toxins on human B cell activation. I. Mitogenic activity of pertussis toxin. Eur. J. Immunol. 20:969–976.
21. Kong, A. S., and S. L. Morse. 1976. The effect of Bordetella pertussis on the antibody response in mice to type III pneumococcal polysaccharide. J. Immunol. 116:989–992.
22. Lagergard, T., J. Shiloaeh, J. B. Robbins, and R. Schneerson. 1990. Synthesis and immunological properties of conjugates composed of group B streptococcus type III capsular polysaccharide covalently bound to tetanus toxoid. Infect. and Immun. 58:687–694.
23. Landsteiner, K. 1935. The specificity of serologic reactions. Harvard University Press, Cambridge, Mass. 24. Lindberg B, J. Lonngren and D. A. Powell. 1977. Structural studies on the specific type-14 pneumococcal polysaccharide. Carb. Res. 58:177–186.
25. Makela, P. H., E. Herva, M. Sibakov, J. Henrichsen, J. Luotonen, M. Leinonen, M. Timonen, M., Koskela, J. Pukander, P. Gronroos, S. Pontynen and P. Karma. 1980. Pneumococcal vaccine and otitis media. Lancet, ii:547–551.
26. Makela, O., V. J. Psanen, H. Sarvas, and M. Lehtonen. 1980. A gene of immunoglobulin H-chain cluster controls the murine antibody response to pneumococcal polysaceharide type 14. Scand. J. Immunol. 12:155–158.
27. Morch, E. 1943. Serological studies on the Pneumococci. Munksgaard, Copenhagen. p. 160.
28. Morse, J. H., A. S. Kong and J. Lindenbaum. 1977. The mitogenic effect of the lymphocytosis promoting factor from *Bordetella pertussis* on human lymphocytes. J. Clin. Invest. 60:683–692.
29. Morse, S. I., and J. H. Morse, 1976. Isolation and properties of the leukocytosis-and lymphocytosis-promoting factor of *Borderella pertussis*. J. Exp. Med. 143:1483–1502.
30. Munoz, J. J., H. Arai, and R. L. Cole. 1981. Mouse-protecting and histamine-sensitizing activities of pertussigen and fimbrial haemagglutinin from *Bordetella pertussis*. Infee. and Immun. 32:243–250.
31. Oda, M., J. L. Cowell, D. G. Burstyn and C. R. Manelark. 1984. Protective activities of the filamentous-hemmaglutinin and the lymphocytosis-promoting factor of *Bordetella pertussis* in mice. J. Infect. Dis. 150:823–833.
32. Olin, P., J. Storsaeter, and V. Romanus. 1989. The efficacy of acellular pertussis vaccine. JAMA. 261:560.

33. Paton, J. C., R. A. Lock, C-J. Lee, J. P. Li, A. M. Berry, T. J. Mitchell, P. W. Andrew, D. Hansman and G. J. Boulnois. 1991. Purification and immunogenicity of genetically obtained pneumolysin toxoids and their conjugation to *Streptococcus pneumoniae* type 19F polysaccharide. Infect. and Immun. 59:2297–2304.

34. Peeters, C. A., A-M. Tenbergen-Meekes, D. E. Evenberg, J. T. Poolman, B. J. M. Zegers and G. T. Rijkers. 1991. A comparative study of the immunogenicity of pneumococcal type 4 polysaccharide and oligosaccharide tetanus toxoid conjugates in adult mice. J. Immunol. 146:4308–4314.

35. Pittman, M. 1975. Determination of the histamine sensitizing unitage of pertussis vaccine. J. Biol. Stand. 3:185–191.

36. Pittman, M. 1979. Pertussis toxin: The cause of the harmful effects and prolonged immunity of whooping cough. A hypothesis. Rev. Infect. Dis. 1:401–412.

37. Pizza, M., A. Covacci, A. Bartoloni, M. Perugini, L. Nencioni, M. T. De Magistris, L. Villa, D. Nucci, R. Manetti, M. Bugnoli, F. Giovannoni, R. Olivieri, J. T. Barbieri, H. Sato, and R. Rappuoli. 1989. Mutants of pertussis toxin suitable for vaccine development. Science. 246:497–500.

38. Porro, M., P. Constantino, S. Fabbiani, V. Pellegrini, and S. Viti. 1984. A semi-synthetic glycoconjugate antigen prepared by chemical glycosylation of pertussis toxin by a meningococcal group C oligosaccharide hapten. Proc. of the Fourth Int. Syrup. on Pertussis. Joint IABS/WHO Meeting, Geneva, Switzerland. Dev. Biol. Stand. 61:525–530.

39. Robbins, J. B., Schneerson, R., Egan W. B., Vann, W., and Liu, D. T. 1980. Virulence properties of bacterial capsular polysaccharides-unanswered questions. Life Sci. Res. Rep. 16:115–13230.

40. Robbins, J. B., R. Austrian, C.-J. Lee, S. C. Rastogi, G. Schiffman, J. Henrichsen, P. H. Makela, C. V. Broome, R. R. Facklam, R. H. Tiesjema and Parke, Jr. 1983. Considerations for formulating the second-generation pneumococcal capsular polysaccharide vaccine with emphasis on the cross-reactive types within groups. J. Infect. Dis. 148:1136–1159.

41. Robbins, J. B., and R. Schneerson. 1990. Polysaccharide-protein conjugates: A new generation of vaccines. J. Infect. Dis. 161:821–832.

42. Sato, Y., H. Arai, and K. Suzuki. 1974. Leukocytosis-promoting factor of *Bordetella pertussis*. III. Its identity with protective antigen. Infec. and Immun. 9:801–810.

43. Sato, H., and Y. Sato. 1984. *Borderella pertussis* infection in mice: Correlation of specific antibodies against two antigens, pertussis toxin and filamentous hemagglutinin with mouse protective activity in an intracerebral or aerosol challenge system. Infect. Immun. 46:415–421.

44. Schiffman, G., R. M. Douglas, M. J. Bonner, M. Robbins, and R. Austrian. 1980. Radioimmunoassay for immunologic phenomena in pneumococcal disease and for the antibody response to pneumococcal vaccine. I. Method for the radioimmunoassay of anticapsular antibodies and comparison with other techniques. J. Immunol. Methods. 33: 130–144.

45. Sekura, R. D., F. Fish, C. R. Manclark, B. Meade and Y-L. Zhang. 1983. Pertussis toxin. Affinity purification of a new ADP-ribosyltransferase. J. Biol. Chem. 258:14647–14651.

46. Sekura, R. D., Y-L. Zhang, R. Roberson, B. Acton, B. Trollfors, N. Tolson, J. Shiloach, D. Bryla, J. Muir-Nash, D. Koeller, R. Schneerson, and J. B. Robbins. 1988. Clinical, metabolic, and antibody responses of adult volunteers to an investigational vaccine composed of pertussis toxin inactivated by hydrogen peroxide. J. Pediatr. 113:806–813.

47. Shapiro, E. D., A. T. Berg, R. Austrian, D. Schroeder, V. Parcells, A. Margolis, R. K. Adair and J. D. Clemens. 1991. The protective efficacy of polyvalent pneumococcal polysaccharide vaccine. N. Eng. J. Med. 325:1453–1460

48. Tamura, M., M. Nogimori, M. Yajima, K. Ase and M. Ui. 1983. A role of the B-oligomer moiety of islet-activation protein, pertussis toxin, in development of the biological effects on intact cells. J. Biol. Chem. 258:6756–6761.

49. Wijgert, J. H. M., A. F. M. Verheul, H. Snippe, I. J. Check and R. K. Hunter. 1991. Immunogenicity of *Streptococcus pneumoniae* type 14 capsular polysaccharide: influence of carriers and adjuvants on isotype distribution. Infect. Immun. 59:2750–2757.

50. Verheul, A. F. M., A. A. Versteeg, M. J. deReuver, M. Janze and H. Snippe. 1989. Modulation of the immune response to pneumococcal type 14 capsular polysaccharide-protein conjugates by the adjuvant quil A depends on the properties of the conjugates. Infect. Immun. 57:1078–1083.

51. Zackrisson, G., J. Taranger and B. Trollfors. 1990. History of whooping cough in nonvaccinated Swedish children, related to serum antibodies to pertussis toxin and filamentous hemagglutinin. J. Pediatr. 116:190–194.

52. Fattom, A., J. Shiloach, D. Bryla, D. Fitzgerald, I. Pastan, W. W. Karakawa, J. B. Robbins, and R. Schneerson. 1992. Comparative immunogenicity of conjugates composed of the Staphylococcus aureus type 8 capsular polysaccharide bound to carrier proteins by adipic acid dihydrazide or N-succinimidyl-3-(2-pyridyldithio) propionate. Infect. and Immun. 60:584–589.

53. Schneerson, R., O. Barrera, A. Sutton, and J. B. Robbins. 1980. Preparation, characterization, and immunogenicity of Haemophilus infiuenzae type b polysaccharide-protein conjugates. J. Exp. Med. 152:361–376.

54. Katz, M. A., S. H. Landesman, and G. Schiffman. 1984. A comparison of antibody concentration measured by mouse protection assay and radioimmunoassay in sera from patients at high risk of developing pneumococcal disease. Mol. Immunol. 21:1061–1065.

55. S. H. Landesman and G. Schiffman, 1981. Assesment of the antibody response to pneumococcal vaccine in high-risk populations. Rev. Infect. Dis. 3 Suppl.:S184–S197.

56. Lawrence, E. M., K. M. Edwards, G. Schiffman, S. H. Sell, J. M. Thompson, W. K. Vaughn, and P. F. Wright. 1983. Pneumococcal vaccination in normal children: primary and secondary vaccination. Amer. J. Dis. Child. 137:846–850.

57. Borgono, J. M., A. A. McLean, P. P. Vella, A. F. Woodhour, A. F. Canepa, W. L. Davidson, and M. R. Hilleman. 1978. Vaccination and revaccination with polyvalent pneumococcal polysaccharide vaccines in adults and infants. Proc. Soc. Exp. Biol. Med. 157:148–154.

SUMMARY OF THE INVENTION

The present invention relates to a synthetic scheme for producing novel conjugates comprising protein, particularly pertussis toxin (PT), chemically bound to saccharides, particularly neutral or non-charged saccharides. The term saccharides encompasses, but is not limited to, polysaccharides and oligosaccharides. The conjugates of the invention are used as immunogens and can provide safe, effective, clinically useful vaccines.

According to the present invention, a protein of important medical value serves as a carder for these saccharides to produce immunogenic conjugate vaccines. More particularly, the present invention is directed to the preparation of conjugate immunogens which comprise PT, and proteins similar to PT, as carrier proteins chemically bound to non-charged or neutral capsular saccharide protective antigens of a bacterial pathogen. The conjugates of the present invention may be considered as haptenated proteins (23, 41). That is, the protein component of the subject invention is a carrier molecule for the saccharide hapten component, thereby rendering the saccharide more immunogenic. The invention includes the synthesis of an antigenic and immunogenic carrier protein-saccharide conjugate product, as well as the use of this product as a potent, non-toxic, and highly immunogenic conjugate vaccine to elicit the production of protective antibodies against both the antigenic protein (e.g. PT) and the pathogenic bacterial saccharide antigen (e.g. Pn14)comprising the synthetic vaccine.

More particularly, the invention is directed to the complete synthesis of a conjugate comprising PT as the carrier protein linked covalently to the neutral Pn14. As mentioned above, the conjugate is referred to as Pn14-PT. In accordance with the present invention, an adipic acid dihydrazide derivative of Pn14 was bound to PT at acidic pH by carbodiimide-mediated condensation. The conjugation procedure rendered PT non-toxic as assayed in vitro by Chinese hamster ovary (CHO) cell assays and in vivo by histamine-releasing activity and lymphocytosis in mice. Inactivated PT is known as detoxified PT or pertussis toxoid. Moreover, the detoxified PT maintained its antigenicity and immunogenicity after the carbodiimide condensation reaction.

According to the present invention, Pn14 was bound to PT so that the resultant Pn14-PT conjugate was found to be immunogenic and non-toxic in mammals, and to elicit both type-specific antibodies to Pn14 and neutralizing antibodies to PT (i.e. antitoxin) at levels estimated to be protective in humans. The Pn14-PT conjugate was evaluated in young outbred mice using a dosage, formulation, immunization route, and immunization schedule that are suitable for clinical use in humans.

The immunologic properties of the novel Pn14-PT conjugate vaccine are described herein. The method of immunization used in the present invention employed about one tenth of the proposed human dosage injected subcutaneously into young recipient animals (e.g. mice) and is predictive of the immunogenicity of the polysaccharide component of other conjugate vaccines in human infants (41). Because the non-toxic Pn14-PT conjugate of the present invention, used at dosages suitable for human immunization, was capable of eliciting protective antibodies to both its PT and Pn14 components in young mammals, it should be an excellent vaccine for clinical use in humans.

According to the present invention, a synthetic scheme is provided to covalently couple a medically important and useful protein, PT, with neutral or non-charged haptenic saccharides (i.e. capsular polysaccharides, oligosaccharides, lipopolysaccharides, and O-specific polysaccharides), most preferably, but not limited to, Pn14, to produce conjugate compounds suitable for use as safe and effective vaccines. The synthetic scheme and resulting conjugates of the invention may also use another medically useful protein with properties similar to those of PT.

In accordance with the present invention and based on the superior immune response in mammals, the immunogenic conjugate of the invention should elicit protective antibodies when introduced into healthy humans, especially infants, as well as adults, thereby affording protection against both the pathogenic carrier protein component of the conjugate and the saccharide component of the conjugate.

It is an objective of the present invention to provide a procedure designed to successfully couple PT, or a similar carrier protein, with a neutral or non-charged saccharide to yield immunogenic conjugates. It is another objective to use the conjugates as substantially non-toxic immunogens to provide protection against bacterial pathogens of infants and children, as well as adults. It is a further objective to elicit, by immunization, protective levels of antibodies directed against both the saccharide and the protein components of the conjugate vaccine of the invention.

Another objective is to employ the conjugate vaccine of the present invention to elicit protective immunity to both pertussis and to diseases, such as pneumonia, meningitis, and otitis media, caused by pneumococcus type 14 or other diseases caused by different, neutral capsulated pathogens.

It is another objective to provide a pharmaceutical composition for use in eliciting protective antibodies and for preventing infection caused by pathogens such as *Bordetella pertussis* and *Streptococcus pneumoniae.*

A further and vital objective is to use the Pn14-PT conjugate vaccine administered as part of a complex vaccine formulation in the routine immunization of all infants and also adults.

DETAILED DESCRIPTION OF THE INVENTION

In view of the universal need for newer and better vaccines to combat harmful infections of infants, children, and adults, the development of the present conjugates, which contain the medically important PT as an effective carrier protein linked to non-charged and medically significant capsular polysaccharides of bacteria, provides a means for preventing such infections by using the present conjugates as vaccines. Indeed, the particular proteinpolysaccharide conjugate vaccines as described herein have vastly improved the immunologic properties of Pn14.

According to the present invention, PT was selected for use as a carrier protein because it is both a virulence factor and a protective antigen of *Bordetella pertussis.* PT may be inactivated by chemical agents or by genetic manipulation (37). In the present invention, the covalent binding of PT to Pn14 to form a conjugate inactivated the toxicity of pertussis toxin, while allowing the detoxified protein to retain its antigenie and immunologic properties. Both PT having toxicity and PT that has been suitably modified, altered, or rendered analogous to the native form, e.g. by chemical, genetic, or molecular techniques or means, and the like, so as to render the PT inactive or non-toxic, are appropriate for use in the coupling method of the present invention, provided that the PT component of the resulting conjugate retains its immunogenicity after coupling to the saccharide component. For isolated or purified PT having toxicity and used as starting material in the present method, the present coupling procedure inactivated the toxin, thereby yielding a non-toxic, yet immunogenic, carrier component of the conjugate product. For use in the method of the present invention, PT may be purified by known procedures or may be obtained commercially.

The present inventors have discovered that the addition of acidic or negatively-charged polysaccharides to soluble PT at pH values of about 4 or less resulted in the formation of an insoluble complex and in the precipitation of both PT and the acidic or negatively-charged polysaccharides. With the exception of, for example, the neutral pneumococcal type 14 and type 7 polysaccharides, and the like, other capsular polysaccharides that are medically important for infants, young children, and adults are negatively-charged and suffer from the problem of insolubility and precipitation when added to PT. Moreover, among the 87 capsular polysaccharides (i.e. serotypes) of *Streptococcus pneumoniae*, pneumococcus type 14 and pneumococcus type 7F are the only two neutral polysaccharides isolated from patients to date (2–4, 27, 40). In addition, the O-specific side chains of lipopolysaccharide from some Gram-negative bacterial pathogens contain neutral saccharides.

The present inventors have found and demonstrated by their invention that at a pH of $\leq 4$ (i.e. at a pH value at which PT is soluble) such as about pH 3.5 to about 4.3, more preferably, at about pH 3.8 to about 4.1, and most preferably at about pH 3.9, and about 4.0, the addition of Pn14 or another non-charged polysaccharide to PT, in solution at about pH $\leq 4$, did not cause precipitation of either the PT or the Pn14. Moreover, according to a unique feature of the present invention, the carbodiimide coupling procedure was performed at low pH, i.e. a pH at which PT is soluble, such as the aforementioned pH ranges, and optimally at pH about 3.9 or about 4.0. The use of low pH in forming the conjugates of the invention is distinct to the present invention, since pH>4 (especially, pH values of about 4.7 to about 5.2), conventionally considered to be optimal for the carbodiimide reaction, rendered PT insoluble. Thus, an important advance and advantage provided by the present invention is that a neutral or non-charged polysaccharide, such as Pn14, Pn7F, and the like, and a generally suboptimal, low pH, namely, pH about 3.9 or about 4.0, were used in the present coupling method to overcome the problems of insolubility and precipitation of the individual components during the process of forming the conjugate. As a result of the present invention, the problems of the insolublity of PT at about pH>4 (and at about neutral pH) and of the precipitation of insoluble complexes of PT with acidic or negatively-charged polysaccharides, have been overcome by the present method which provides suitable conditions, heretofore unknown, for coupling PT, and similar proteins, with Pn14, and the like.

The present invention provides a method and conditions for preparing a synthetic and medically useful conjugate containing PT, and the like, and a neutral polysaccharide, namely, Pn14, which can be used as a safe, effective, non-toxic, and potent vaccine in humans.

As described above, the method overcomes the vexing and unusual solubility and precipitation problems which ordinarily accompany the use of PT under conditions different from those described in the present invention. Successful production of the carrier proteinpolysaccharide conjugates of the present invention involves the use of low pH and a neutral (non-charged) polysaccharide under the described conditions of the method.

In one aspect of the invention, a method for producing conjugate compounds by covalently linking PT to neutral Pn14, or another non-charged saccharide, has been devised so as to preserve the immunogenicity of the native protein and to enhance the immunogenicity of the saccharide component. To this end, the polysaccharide was first activated by using cyanogen bromide, followed by reaction with a suitable linker molecule, preferably, but not limited to, adipic acid dihydrazide. Other types of useful linkers are well known in the art, for example, N-succinimidyl-3-(2-pyridyldithio) propionate. The Pn 14-adipic acid dihydrazide derivative and the PT were solubilized at pH about 3.9 to about 4.0, mixed, and coupled in the presence of 1-ethyl-1,3-(3-dimethylaminopropyl) carbodiimidehydrochloride at pH about 3.9 to about 4.0. The reaction mixture was subjected to gel filtration and the Pn14-PT conjugate compound was collected in the void volume fractions. The method of the present invention, in which the coupling reaction of PT and derivatized Pn14 was performed at acidic pH, allowed PT to be used as a carrier, in spite of the aforementioned disadvantageous properties of PT when PT is introduced at non-acidic or neutral pH.

In one embodiment, the Pn14-PT conjugate was used as an effective immunogen in young outbred mice using a priming and boosting immunization regimen in the absence of adjuvant such that a total of three injections given at two week intervals resulted in enhanced protective immunity to both the Pn14 and the PT antigens, including the production of PT antitoxin.

In another embodiment, the Pn14-PT conjugate was used as a vaccine and was injected at effective doses based on polysaccharide content, for example, about 2.5 $\mu$g of polysaccharide per injection, three times at two week intervals. The amount of the polysaccharide used in the conjugate vaccine was determined by subjecting the sample solution containing the polysaccharide to colorimetric analysis (e.g. Anthrone reaction). The colorimetric reaction results were compared with a standard curve generated by using known amounts of the polysaccharide. The appropriate dilution of the sample was then made to contain the final amount of polysaccharide as used in the immunizing dose. The amount of protein in the conjugate varied as described hereinbelow and was determined by the Lowry reaction. The 2.5 $\mu$g dose of Pn14 in the Pn14-PT conjugate in an approximately 20 g mouse is approximately ten percent of a proposed human dose. It will be appreciated that if a fraction of the human dose, e.g. 2.5 $\mu$g, elicited protective immunity in mice, which are much less responsive than humans to the polysaccharide component of the vaccine, then at similar dosage levels and at levels which are approximately 10-fold higher (e.g. about 2.5 $\mu$g to at least about 50 $\mu$g) than those used in mice, the vaccine is expected to produce significant levels of protective antibodies in immunized humans. As used in the present invention, the conjugate vaccine elicited protective levels of antibodies to PT and Pn14 in recipient mammals and stimulated the production of neutralizing antibodies to the PT carrier protein.

As a result of the present method, the Pn14-PT vaccine had the ability to increase the immunogenicity of the bacterial polysaccharide. In contrast to the slight or undetectable serum antibody response induced by Pn14 polysaccharide in laboratory mice, the conjugate of the present invention induced high levels of antibodies in almost all recipients. In addition, the conjugates elicited statistically significant rises of antibodies to the PT and Pn14 after the second or booster injection. This heightened response to the Pn14 and PT is characteristic of a T-cell dependent immune response. Thus, the present invention increased the immunogenicity of the Pn14 polysaccharide and conferred upon it the properties of a T-dependent antigen.

Using the present method to create a conjugate vaccine, the immunologic properties of the non-toxic protein, as a component of the conjugate, were effectively retained, at the same time that the immunogenicity of the saccharide component was significantly enhanced. Both components of the vaccine stimulated levels of antibodies that have been correlated with protective immunity against the diseases caused by the two pathogens.

The vaccine of the invention is typically formed by dispersing the conjugate in a suitable pharmaceutically-acceptable solution such as physiological saline or other injectable liquids. The vaccine is generally and preferably administered parenterally, usually via subcutaneous or intramuscular routes of injection. For parenteral administration, the conjugate may be in sterile solution or suspension or may be emulsified in pharmaceutically- and physiologically-acceptable aqueous or oleaginous vehicles, which may contain preservatives and material for rendering the solution or suspension isotonic with body fluids (i.e. blood) of the recipient. Such formulations may be used in unit-dose or in multi-dose containers for convenience. A pharmaceutically-acceptable vaccine formulation including an acceptable diluent or excipient in conjunction with the conjugate compounds of the present invention comprise a pharmaceutical composition of the present invention. For example, excipients suitable for use are water, phosphate buffered saline, pH 7.4, 0.15M aqueous sodium chloride solution, dextrose, glycerol, dilute ethanol, and the like, and mixtures thereof. The vaccine may be administered either intravenously, intraperitoneally, or orally.

If oral administration is desirable or required, the vaccine may be presented as a draught in water or in a syrup, in capsules, cachets, boluses, or tablets, as a aqueous or oleaginous solution or suspension or a suspension in a syrup. Such suspensions optionally may include suspending agents, or may be presented as an oil-in-water or water-in-oil emulsion. Where desirable or necessary, flavoring, sweetening, preserving, emulsifying, or thickening agents may be included in the formulation. Additional formulations suitable for other modes of administration such as suppositories may include binders and carders, for example, polyalkalene glycols or triglycerides.

Tablets may contain the conjugate preparation as a powder or granules, for example, a lyophilized powder or granules optionally mixed with binders, lubricants, inert diluents, or surface-active or dispersing agents, and may be formed by compression or by mouling in inert liquid diluent. Such tablets may be optionally scored and/or coated. Capsules and cachets may contain the active conjugate compound alone or in admixture with one or more accessory ingredients. Capsules may also contain the active conjugate in aqueous or oleaginous solution, suspension, or emulsion, optionally in association with accessory ingredients.

In general, the conjugate vaccines of the present invention are formulated so that the antigens are present in solution at a dose of from about 2.0 $\mu$g to about 100 $\mu$g, preferably, at about 2.5 $\mu$g to about 50 $\mu$g, and more preferably at about 10 $\mu$g to 50 $\mu$g in a total volume of about 0.1 mL to about 1.0 mL, preferably about 0.5 mL. Naturally, the optimal dosage to be administered is determined by dose-response experimentation. Presented in unit dosage form, each dose may be conveniently contained in, but is not limited to being contained in, volumes of from about 0.1 mL to about 1.0 mL, preferably about 0.5 mL. It is generally preferred that each dose contains from about 2.5 $\mu$g to about 50 $\mu$g of the polysaccharide in a volume of about 0.5 mL. It will be appreciated that the relative proportions of PT or similar protein and neutral sacchafide may be varied in the vaccine and the vaccine remains safe, effective, and immunogenic. For example, for the conjugates of the present invention used on a mass basis (e.g. w/w), equal amounts of protein and polysaccharide may be used in the conjugate vaccine, and up to about 10 times more protein than polysaccharide, preferably about 3 to about 6 times more protein than polysaccharide, was acceptable for use in the conjugate vaccine.

If desired or necessary, although not mandatory, the conjugate vaccine of the invention is administered or formulated with a customary stabilizer such as sorbitol or lactose and an effective dosage of one or more adjuvants or immunopotentiating agents, for example, aluminum phosphate, aluminum hydroxide (e.g. Alhydrogel), aluminum sulfate, muramyl dipeptide (MDP), or one of its derivatives, monophosphoryl lipid A (MPL), or purified Saponin (Quil-A).

The conjugate vaccine of the present invention may be administered to human beings to prevent whooping cough and any of the diseases associated with infection by *Streptococcus pneumoniae*, and may be formulated with the components of other vaccines to prevent a variety of pediatric and adult diseases and infections in accordance with any vaccination schedule suitable for vaccination against such diseases. The dosage administered and schedule used depend on the antigenicity and immunogenicity of the antigens in the conjugate and on other known pharmaceutical considerations such as the age and body weight of the individual. A recommended vaccination schedule provides the vaccine at two to six months of age in at least two doses separated by an interval of from four to six weeks, preferably followed by a booster dose at about fifteen months and again at about five years of age. The vaccine of the present invention may also be formulated with other vaccines designed to prevent diseases of adults. The number of doses may be reduced by at least some extent, depending on the degree of immunopotentiation resulting from the conjugate vaccine of the present invention.

In summary, the synthetic conjugates of the present invention, heretofore unable to be attained until the present discoveries were made, offer abundant, safe, highly effective, and immunologically protective vaccines for infants, children, and adults.

EXAMPLES

The invention is further demonstrated by, but not limited to, the following illustrative examples:

EXAMPLE 1

MATERIALS AND METHODS

Reagents

Pn14 was supplied by Dominique Schulz, Pasteur Merieux Vaccins and Serums, Lyon, France. Pn14 can be purified using published methods and can be obtained commercially. Pertussis toxin was prepared as previously described (45). It was stored as a 90% ammonium sulfate precipitate at 3° C. to 8° C. Murine monoclonal antibodies to PT, 1015-6FX1 and 1014-3CX4, were donated by James Kenimer, CBER, Food and Drug Administration. Rabbit anti-pneumococcus type 14 antibody (Lederle Laboratories, Pearl River, N.Y.), cyanogen bromide (Kodak, Rochester, N.Y.), acetonitrile (high pressure liquid chromatography grade; Fisher Scientific Co, Springfield, N.J.), adipic acid dihydrazide (ADH) and 1-ethyl-l,3-(3-dimethylaminopropyl) carbodiimide (EDAC; Sigma Chemical Co., St. Louis, Mo.), and 2,4,6-trinitrobenzene sulfonic acid (TNBS; Pierce Chemical Co, Rockford, Ill.) were used as reagents.

Analyses

Polysaccharide was measured by the anthrone reaction with Pn14 as a standard (15). Adipic acid hydrazide (AH) was measured by the 2,4,6-trinitrobenzene sulfonic acid reaction with adipic acid dihydrazide as a standard (10). Protein was measured by the Lowry reaction with bovine serum albumin as a standard (10). Some of the lots of Pn14-PT were adsorbed onto Alhydrogel (Superfos, Copenhagen, Denmark) at 0.1 mg aluminum per 0.1 ml of conjugate containing 2.5 ug of saccharide.

Synthesis of Pn14-PT conjugates

Pn14 was derivatized with adipic acid dihydrazide; the degree of derivatization was 2.0% (w/w) (19). For derivatization, Pn14 was converted into sodium salt by passage through Dowex 50W×8 (14) or by other methods known in the art, activated with cyanogen bromide (Eastman Chemical Products, Rochester, N.Y.) at pH 10.5 for 6 minutes, and reacted with 0.5M ADH dissolved in 0.5M sodium bicarbonate by tumbling overnight at 3° C. to 8° C. The reaction mixture was dialyzed against 0.2M NaCl with two changes for 24 hours, followed by gel filtration through 4B-Cl Sepharose equilibrated in 0.2M NaCl, dialyzed against water, and freeze-dried.

The Pn14-adipic acid hydrazide derivative was dissolved in water, and the pH was brought to about 3.9 with 0.1M HCl. PT, stored as a precipitate in 90% saturated ammonium sulfate solution, was dialyzed against 0.5M sodium acetate, about pH 3.9, at 3° C. to 8° C. The Pn14-adipic acid hydrazide derivative and PT were brought to a final concentration of approximately 5.0 mg/ml each in the reaction mixture. 1-ethyl-1,3-(3-dimethylaminopropyl) carbodiimide (EDAC) was added to a concentration of 0.1M and the pH of the mixture was maintained at about 3.9 for 4 hours at room temperature for Pn14-PT (A) and at 3° to 8° C. for Pn14-PT (B). Each reaction mixture was dialyzed against 0.5M sodium acetate, about pH 3.9, and applied to a column (1 by 90 cm) of Bio-Gel P-300 in that buffer. The void volume fractions or samples, containing the Pn14-PT conjugate, were made 0.01% in thimerosal.

A portion of Pn14-PT (A) was adsorbed onto Alhydrogel (Superfos, Copenhagen, Denmark) at 0.1 mg of aluminum per 0.1 ml of conjugate containing 2.5 μg of saccharide. This adsorbed conjugate was denoted as Pn14-PT (C). The protein/saccharide ratio (w/w) of the three conjugates was approximately 5.5.

The third conjugate, Pn14-PT (C), was further treated (see Table 2). One portion was mixed with saturated ammonium sulfate to a final concentration of 90% at 4° C., left overnight at 3° C. to 8° C., and centrifuged for 30 minutes at 15,000× at 4° C. The resulting precipitate (D) and the supernatant (E) were dialyzed against phosphate buffered saline. Another portion of Pn14-PT (C) was passed through a column (1 by 90 cm) of P-300 in 0.5M sodium acetate-1% sodium dodecylsulfate (SDS), and the void volume (F) was used for immunization. Most of the PT in this preparation emerged in the void volume of the P-300 column.

Serologic testing

Serum antibodies to Pn14 were measured by radioimmunoassay and amounts were expressed as ng antibody nitrogen per milliliter of serum (44). Serum antibodies to PT were measured by enzyme-linked immunosorbant assay (ELISA) and by inhibition of the effect of the toxin on Chinese hamster ovary (CHO) cells (17, 46, 51). Antibody amounts were expressed as units referable to a given serum standard.

Assay of pertussis toxin

The histamine-sensitizing activity of PT and of the Pn14-PT conjugates was assayed as described previously (16, 35). In this assay, about 80 ng per mL of PT caused a statistically significant decrease in the $LD_{50}$ of histamine in mice, while about 60-61 μg per mL of the detoxified Pn14-PT conjugate had no effect. The in vitro toxicity of PT was assayed with CHO cells (16); 1.5 ng/mL could be detected by the CHO method. The toxicity of the Pn14-PT conjugates was reduced about six thousand-fold as determined by the CHO cell assay.

Immunization

General purpose female mice from the National Institutes of Health colony, approximately 5 weeks old, were injected subcutaneously with the Pn14-PT conjugates in saline solution, without adjuvant, three times at biweekly intervals. Forty mice were used in each experiment and thirty mice were injected with each preparation. Ten animals were exsanguinated two weeks after the first injection, and one week after the second and third injections. From the results presented in Tables 1 and 2 and detailed in Example 3 hereinbelow, the above-described Pn14-PT (A) and Pn14-PT (B) conjugates were the most effective immunogens, although protective antibodies were also detected using the other conjugate preparations. The 2.5 μg of polysaccharide dose per dose in the conjugate was used on the basis of previous work and because this amount of polysaccharide in the conjugate was considered to be compatible with dosages proposed to be acceptable in humans, including infants. Based upon the successful use of polysaccharide conjugates in human infants and the evaluation of these conjugates in mice, proposed dosages for human infants range from about 2.5 μg to about 50 μg (41).

Statistics

Data analysis was performed by using the Statistical Analysis System (SAS). The logarithms of the concentrations were used for all calculations. Antibody concentrations below the sensitivity of the ELISA and the CHO assay were assigned values equal to one-half the threshold value. For comparison of the geometric means, the unpaired t test was used.

EXAMPLE 2

Pneumococcus type 14 antibodies

The preimmunization serum samples of the mice contained trace or non-detectable levels of antibodies to Pn14. In the two experiments, injection of 2.5 μg of Pn14 alone did not elicit serum antibody responses. The Pn14-PT conjugates in saline, containing 2.5 μg saccharide, elicited statistically significant antibody increases after the first two injections (see Tables 1 and 2). The third injection of Pn14-PT did not elicit an elevation in the level of Pn14 antibodies. There were no differences between the levels of Pn14 antibodies elicited by the conjugate prepared at 3° C .to 8° C. (A) and by the conjugate prepared at room temperature (B). Addition of alum, which served as adjuvant, to the Pn14-PT conjugates did not enhance the antibody responses to either Pn14 or PT (Pn14-PT (C) in Table 1).

The levels of pneumococcal antibodies estimated to be protective have been reported (54, 55).

EXAMPLE 3

Pertussis toxin antibodies

Antibodies to PT were not detected in the preimmunization serum samples. Pn14-PT conjugates, denoted (A) and (B), elicited significant rises ($P < 0.0001$) of PT antibodies after both the first and second injections (Table 1 and 2).

TABLE 1

Serum antibodies elicited in mice by Pn14-PT conjugates[a]

Geometric mean antibody conc[b] (25th–75th centiles)

| Immunogen | n | After first injection Pn 14 | PT | After second injection Pn14 | PT | After third injection Pn 14 | PT |
|---|---|---|---|---|---|---|---|
| Pn14 PS | 8 | 3.3a (1.2–5.9) | 0.05f (0.05) | 6.0 (4.37–10.9) | 0.05f (0.05) | 12.7 (8.11–16.3) | 0.05f (0.05) |
| Pn14-PT (A) | 10 | 188b (89.8–521) | 106g (79–147) | 1,772d (1,653–1,974) | 965h (308–2,201) | 1,642 (1,478–1,783 | 1,496 (800–2,921) |
| Pn14-PT (B) | 11 | 289b (111–860) | 107g (69–216) | 1,747d (1,553–2,074) | 905h (539–1,843) | 1,932 (1,813–2,187) | 1,448 (1,143–1,775) |
| Pn14-PT (C)[c] | 11 | 607c (512–881) | 94g (68–129) | 1,488c (1,302–1,636) | 644h (421–1,156) | 1,274 (846–1,759) | 1,059 (700–1,715) |

[a]Five week-old female general-purpose mice were injected at biweekly intervals with 2.5 μg of Pn14 alone or as a conjugate and exsanguinated 14 days after the first injection or 7 days after either of the last two injections. Pn14 antibodies were measured by radioimmunoassay (nanograms of antibody nitrogen per (milliliter) (44) PT antibodies were measured by ELISA and expressed as units (17, 46). Levels of preimmune Pn14 antibodies were 5.39 ng of antibody nitrogen per mL, and PT antibodies were not detectable in preimmune serum.
[b]$P = 0.0001$ for c, b versus a, d versus b; g versus f, and h versus g. $P = 0.002$ for c versus c).
[c]Pn14-PT (A) adsorbed onto Alhydrogel.

TABLE 2

Serum antibodies elicited in mice by Pn14-PT conjugates[a]

Geometric mean antibody concn (25th–75th centiles)

| Immunogen | n | After first injection Pn14 | PT | After second injection Pn14 | PT | Antitoxin |
|---|---|---|---|---|---|---|
| Pn14 CP | 8 | 3.13a (1.0–1.8) | 0.05 | 4.08a (1,128–1,494) | 0.05 | <10 |
| Pn14-PT (A) | 9 | ND[b] | ND | 1,303c (1 128–1,494) | 2,928 (1,738–4,523) | 346 |
| Pn14-PT (D) | 10 | 102b (33.3–324) | 0.26 (0.05–1.00) | 1,269c (1,047–1,485) | 36.8 (15.7–219) | <10 |
| Pn14-PT (E) | 10 | 266b (128–216) | 172 (122–253) | 1,292c (1,125–1,524) | 1,098 (833–1,897) | 80 |
| Pn14-PT (F) | 10 | 156b (48.5–439) | 0.25 (0.05–0.52) | 1,237c (1.071–1,403) | 1.41 (0.50–2.73) | <10 |

[a]Five week-old female general-purpose mice were injected at biweekly intervals with 2.5 μg of Pn14 alone or as a conjugate and exsanguinated 14 days after the first injection or 7 days after either of the last two injections. Pn14 antibodies were measured by radioimmunoassay (nanograms of antibody nitrogen per milliliter) (44) PT antibodies were measured by ELISA and expressed as units (17, 46). Preimmune Pn14 antibody levels were 5.39 ng of antibody nitrogen per ml. PT antibodies were not detectable in preimmune serum.
[b]ND, not done.

The present invention demonstrated that covalent attachment of Pn14 to PT protein conferred both enhanced immunogenicity and T-cell dependence (booster responses), thereby rendering the Pn14 a T-dependent antigen.

PT was chosen as a carrier in the present invention because the Pn14-PT conjugate has the potential for inclusion in the vaccines used for routine immunization of infants (e.g. Diphtheria-Tetanus-Pertussis (DTP)) and because antibodies to Pn14 and PT confer protective immunity to pneumococcal infection and to pertussis, respectively. Strains of Pn14 used alone are non-pathogenic for laboratory mice (27) (i.e. inocula of $\geq 10^6$ are required to achieve a lethal effect). The presence of protective levels of serum antibodies to Pn14, as well as to other pneumococcal capsular polysaccharides, is predictive of protective immunity in humans.

The rise in antibody levels after the third injection was not statistically significant. Adsorption of the Pn14-PT onto alum (Pn14-PT (C), Table 1) had no significant effect upon the antibody responses to Pn14 or to PT. Table 2 shows that precipitation of the Pn14-PT with ammonium sulfate or treatment with SDS significantly reduced the serum antibody responses to the PT but not to the Pn14 component of the conjugate. However, Pn14-PT (E) (supernatant of the ammonium sulfate precipitation) elicited antibody responses to Pn14 and PT, similar to those of the untreated conjugates.

Table 2 shows the neutralizing activity of PT antibodies elicited by the Pn14-PT (A), (D), (E), and (F). Although one injection of these conjugates did not elicit antitoxin, Pn14-PT (A) elicited a geometric mean (GM) antibody concentration of 346 U following the second injection. After precipitation with ammonium sulfate, the resolubilized precipitate, Pn14-PT (D), did not elicit antitoxin, whereas the supernatant, Pn14-PT (E), elicited a GM of 80 U. Pn14-PT (F), exposed to 1% SDS, also failed to elicit antitoxin.

Clinical studies have shown that there is a good correlation between the levels of antitoxin and PT antibodies measured by ELISA (46). There is also evidence that demonstration of neutralizing activity of pertussis antibodies by the CHO cell assay is predictive of protective immunity to pertussis (51 ). Thus, the CHO cell assay stands as a good candidate for standardizing acellular vaccines containing PT.

PT exerts diverse pharmacologic actions, including modulation of the serum antibody response to polysaccharides (20, 21). Many of these actions require the enzymatic function of the A subunit of PT (8, 48). In the present invention, the preparations of Pn14-PT were not toxic to CHO cells which are sensitive to the A subunit of PT (9, 48). Also, at about 60 to 61 μg/mL, the Pn14-PT conjugates of the invention were not active in the histamine sensitization assay which can detect about 80 ng/mL of PT (35, 46). The toxicity of the PT in the present invention was reduced approximately $6 \times 10^3$-fold as determined by the CHO cell assay.

The method of immunization of the present invention employed approximately one tenth of the dosage which can potentially be used in humans and was injected subcutaneously without adjuvants into young outbred mice. Such an immunization protocol has been predictive of the immunogenicity of the polysaccharide component of other conjugate vaccines in human infants (41). However, other suitable dosages, formulations, and immunization routes and schedules may be employed, and appropriate adjuvants may be used in conjunction with the conjugates, if necessary or desired. Because the synthetic scheme of the present invention provided a means for a medically important, yet insoluble or poorly soluble protein, PT, and similar proteins, to be coupled to medically important capsular saccharides of bacteria, the conjugates of the invention were successfully produced and used. The present method yielded non-toxic and immunogenic conjugates capable of eliciting protective antibodies to both the Pn14 and PT components of the conjugate at doses suitable for producing a response in experimental mammals, including humans. Consequently, the novel conjugate vaccine of the present invention is most appropriate for clinical use in human recipients.

The publications mentioned hereinabove are incorporated in their entirety by reference.

Although the foregoing invention has been described in some detail by way of illustration and example for purposes of clarity of understanding, it will be obvious to those skilled in the art that certain changes and modifications may be practiced without departing from the true spirit and scope thereof, as described in the specification and defined in the appended claims.

What is claimed is:

1. A method for preparing a pertussis toxin carrier protein and polysaccharide conjugate compound, comprising the steps of:
   (a) providing:
      (i) said pertussis toxin carrier protein, and
      (ii) a neutral or non-charged capsular polysaccharide;
   (b) derivatizing said capsular polysaccharide with a linker molecule;
   (c) solubilizing said pertussis toxin protein and said derivatized capsular polysaccharide at a pH of about 3.5 to about 4; and
   (d) coupling said pertussis toxin protein and said polysaccharide from step (c) with carbodiimide at a reaction pH of about 3.5 to about 4, resulting in the covalent coupling of said pertussis toxin protein and said polysaccharide to form said carrier protein and capsular polysaccharide conjugate compound.

2. The method according to claim 1, wherein the pH in steps (c) and (d) is about 3.9.

3. The method according to claim 1, wherein said neutral or non-charged capsular polysaccharide of step (a)(ii) is selected from the group consisting of pneumococcus type 14 capsular polysaccharide of *Streptococcus pneumoniae* type 14 (Pn14), pneumococcus type 7 capsular polysaccharide of *Streptococcus pneumoniae* type 7 (Pn7), and O-specific lipopolysaccharide side chains of Gram-negative bacteria.

4. The method according to claim 3, wherein said capsular polysaccharide is pneumococcus type 14 polysaccharide of *Streptococcus pneumoniae* type 14 (Pn14).

5. Pertussis toxin and neutral capsular polysaccharide conjugate produced by the method according to claim 1.

6. Pertussis toxin and neutral capsular polysaccharide conjugate produced by the method according to claim 2.

7. Pertussis toxin and neutral capsular polysaccharide conjugate produced by the method according to claim 3.

8. Pertussis toxin and pneumonococcus type 14 capsular polysaccharide of *Streptococcus pneumoniae* type 14 (Pn14) conjugate produced by the method according to claim 4.

9. A pharmaceutical composition comprising said conjugate according to claim 8 in a pharmaceutically acceptable carrier, diluent, or excipient.

10. A vaccine comprising said pharmaceutical composition according to claim 9.

11. The method according to claim 1, wherein the linker molecule in step (b) is adipic acid dihydrazide.

* * * * *